US00PP10841P

United States Patent [19]

Grant et al.

[11] Patent Number: Plant 10,841

[45] Date of Patent: Mar. 30, 1999

[54] RUELLIA PLANT NAMED 'COLOBE PINK'

[75] Inventors: Greg Grant, Center; Agnes Hubbard, Fair Oaks Ranch; James Spivey, Devine, all of Tex.

[73] Assignee: Color Spot Nurseries, Inc., Pleasant Hill, Calif.

[21] Appl. No.: 940,113

[22] Filed: Sep. 29, 1997

[51] Int. Cl.[6] ..... A01H 5/00

[52] U.S. Cl. ..... Plt./54.1

[58] Field of Search ..... Plt./54.1, 68.1

*Primary Examiner*—Howard J. Locker
*Assistant Examiner*—Kent L. Bell
*Attorney, Agent, or Firm*—C. A. Whealy

[57] ABSTRACT

A distinct cultivar of Ruellia plant named 'Colobe Pink', characterized by its compact plant habit; numerous soft pink flowers with a purple eye; flowers held above the foliage; moderately vigorous growth habit; durable dark green foliage; and high temperature and high light tolerance.

2 Drawing Sheets

The present invention relates to a new and distinct cultivar of Ruellia plant, botanically known as *Ruellia brittoniana,* and hereinafter referred to by the cultivar name 'Colobe Pink'.

The new cultivar is a product of a planned breeding program conducted by the inventors in San Antonio, Tex. The objective of the breeding program was to develop compact, pink-flowered Ruellias with flowers held above the foliage.

The new cultivar originated from a cross made by the inventors of two distinct proprietary selections of *Ruellia brittoniana*. The cultivar 'Colobe Pink' was discovered and selected by the inventors in March, 1997, as a flowering plant within the progeny of the stated cross in a controlled environment in San Antonio, Tex.

Asexual reproduction of the new cultivar by stem cuttings taken in San Antonio, Tex., has shown that the unique features of this new Ruellia are stable and are reproduced true to type in successive propagations.

The cultivar 'Colobe Pink' has not been observed under all possible environmental conditions. The phenotype may vary somewhat with variations in environment such as temperature, light intensity, and fertility level, without, however, any variance in genotype.

The following traits have been repeatedly observed and are determined to be the unique characteristics of 'Colobe Pink'. These characteristics in combination distinguish 'Colobe Pink' as a new and distinct cultivar:

1. Compact and rounded plant habit.
2. Numerous soft pink flowers with a purple eye.
3. Flowers held above the foliage.
4. Moderately vigorous growth habit.
5. Durable dark green foliage.
6. High temperature and high light tolerant.

Plants of the new Ruellia are similar in size to plants of the *Ruellia brittoniana* cultivar 'Katie ' (not patented). However in side-by-side comparisons conducted in San Antonio, Tex., plants of the new Ruellia had more flowers, flowered earlier, and held flowers higher above the foliage than plants of the cultivar 'Katie'. In addition, the flower color of plants of the cultivar 'Katie' is blue purple whereas the flower color of plants of the new Ruellia is soft pink.

Plants of new Ruellia are similar in flower color to plants of the *Ruellia brittoniana* cultivar 'Chi Chi' (not patented). However in side-by-side comparisons conducted in San Antonio, Tex., plants of the new Ruellia were much more compact. In addition, plants of the cultivar 'Chi Chi' have weak peduncles and flowers tend to droop whereas plants of the new Ruellia have strong peduncles and hold flowers upright and outward.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the first sheet comprises a side perspective view of a typical plant of the cultivar 'Colobe Pink'.

The photograph at the bottom of the first sheet comprises a close-up view of typical flowers of the cultivar Colobe Pink.

The photograph on the second sheet comprises a close-up view of a typical flower bud (1), open flower(2), and leaf(3) of the cultivar 'Colobe Pink'. Flower and foliage colors in the photographs may appear different than the actual colors due to light reflectance, most apparent in the bottom photograph of sheet one.

DETAILED BOTANICAL DESCRIPTION

The following observations and measurements describe plants grown during the spring and summer in San Antonio and Keller, Tex. under full sun or under 30 percent light reduction from polypropylene shadecloth. Day temperatures ranged from 10° to 38° and night temperatures ranged from 4° 27° C.

In the following description, color references are made to The Royal Horticultural Society Colour Chart except where general terms of ordinary dictionary significance are used.

Botanical classification: *Ruellia brittoniana* cultivar 'Colobe Pink'.

Parentage:

*Male, or pollen parent.*—Proprietary selection of *Ruellia brittoniana.*

*Female, or seed parent.*—Proprietary selection of *Ruellia brittoniana.*

Propagation:

*Type cutting.*—Stem cuttings taken from new growth.

*Time to initiate roots.*—Summer: About 7 days at temperatures of 29° to 35° C. Winter: About 10 days at temperatures of 16° to 21° C.

*Time to develop roots.*—Summer: About 15 days at temperatures of 29° to 35° C. Winter: About 18 days at temperatures of 16° to 21° C.

*Rooting habit.*—Vigorous, numerous, fibrous; main roots, thick; laterals, fine, freely branching.

Plant description:

*Form.*—Rounded and compact herbaceous subshrub.

*Production time.*—From a rooted cutting, usually 6 to 11 weeks are required to produce a finished plant in a one-gallon container. Production time will depend on actual environmental conditions and cultural treatments employed.

*Branching habit.*—Freely branching. Removal of the terminal apex (pinching) stimulates development of lateral branches.

*Plant height.*—About 22 cm.

*Plant width.*—About 37 cm.

*Vigor.*—Moderate.

*Lateral stem description.*—Internode length: About 5 mm. Diameter: About 1 cm. Texture: Glabrous. Color: 143A.

*Foliage description.*—Leaves single, whorled, generally symmetrical, durable and long-persisting. Length: About 13.5 cm. Width: About 1.75 cm. Shape: Linear. Apex: Acuminate. Base: Attenuate, sessile. Margin: Irregular, mostly entire. Texture: Glabrous, smooth and leathery. Veins prominent. Durability: Very durable. Color: Young leaves, upper surface: 147A. Young leaves, lower surface: 147B. Mature leaves, upper surface: Darker than 147A. Mature leaves, lower surface: Slightly lighter than 147A. Venation, upper surface: Darker than 147A. Venation, lower surface: 147B.

Flower description:

*Flower type and habit.*—Single flowers with 5-parted corolla and funnelform throat. Calyx five-parted. Flowers arranged in axillary compound cymes. Flowers face upward and/or outward. Freely flowering, usually at least 20 flowers open simultaneously.

*Natural flowering season.*—Spring through fall.

*Flower longevity.*—Flowers open quickly and usually last about one day. Flowers self-cleaning.

*Fragrance.*—None.

*Flower diameter.*—About 5.25 cm.

*Flower depth (height).*—About 3 cm.

*Petals.*—Appearance: Thin, translucent, crepe. Quantity: Five fused at base. Length: About 4.75 cm. Width: About 2 cm. Aspect: Flat or slightly recurved. Shape: Elliptical. Apex: Rounded to notched. Margin: Irregular, mostly entire. Color: Upper surface: 65A, color fades to 65B/65C with development. Lower surface: 65B. Throat: 71A. Tube: 75A.

*Pedicel.*—Aspect: Straight. Strength: Flexible, but strong. Length: About 5 mm. Color: 143A.

*Flower bud.*—Shape: Elongated. Rate of opening: Rapid. Length: About 3 cm. Diameter: About 7.5 mm. Color: Typically whitish green with pink tinge.

*Calyx.*—Shape: Star of five sepals fused at base. Length: About 1 cm. Diameter: About 3 mm. Sepal shape: Linear, narrow. Sepal apex: Acuminate. Sepal margin: Entire. Sepal texture: Slightly pubescent. Color, both surfaces: Close to 147A.

*Reproductive organs.*—Androecium: Stamen number: Four. Filament length: About 2 cm. Filament color: White. Anther shape: Oblong, narrow. Anther size: About 3 mm by 1 mm. Anther color: White. Amount of pollen: Moderate to abundant. Pollen color: White. Gynoecium: Pistil length: About 2.25 cm. Style color: Whitish green. Stigma color: White.

Disease resistance: The new Ruellia has been observed to be resistant to pathogens common to Ruellia.

Seed production: Seed production has been observed. Seed characteristics are typical of the species.

It is claimed:

1. A new and distinct cultivar of Ruellia plant named 'Colobe Pink', as illustrated and described.

* * * * *

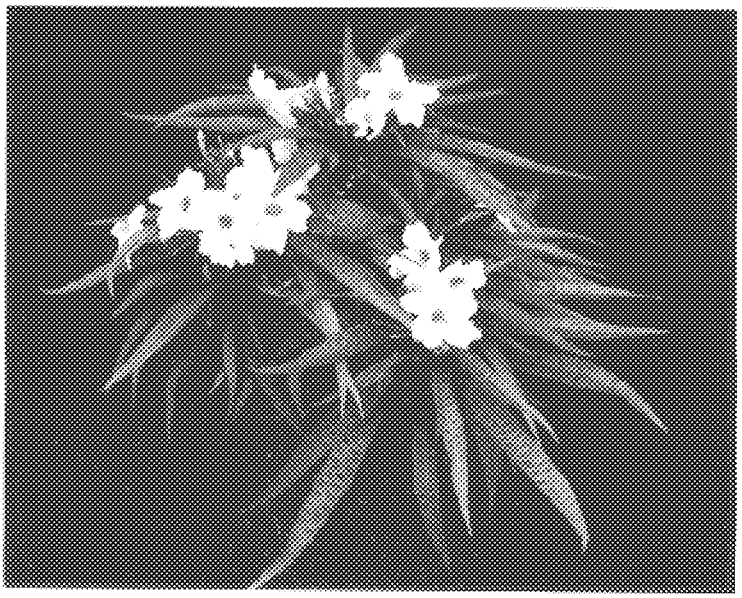
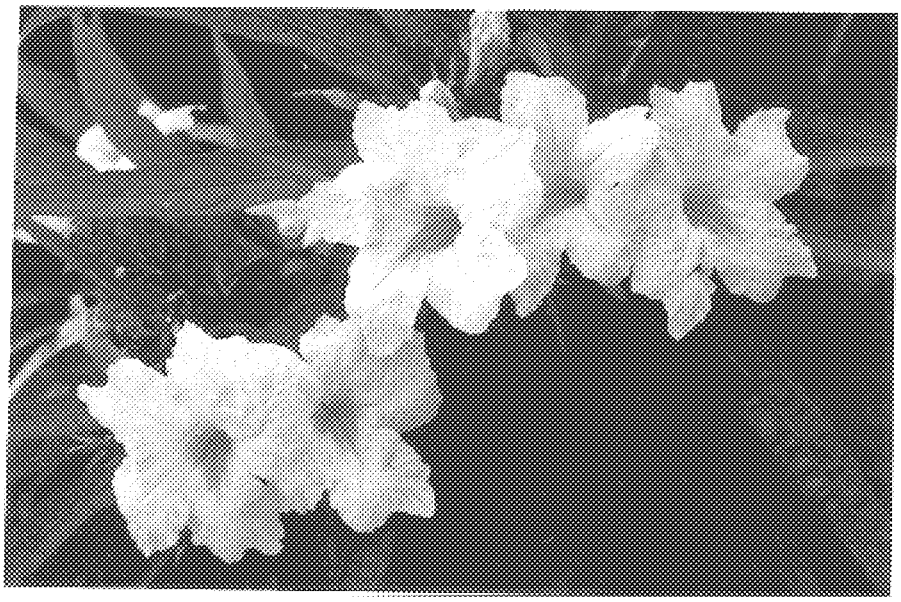

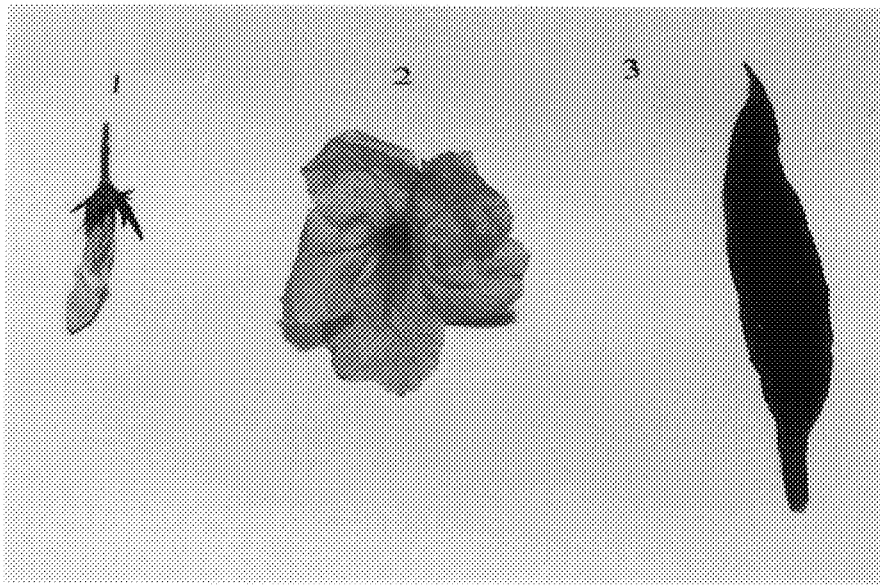
1
2
3